(12) United States Patent
Schmitt et al.

(10) Patent No.: US 10,251,913 B2
(45) Date of Patent: Apr. 9, 2019

(54) USE OF WHEY PROTEIN MICELLES AND POLYSACCHARIDES FOR IMPROVING INSULIN PROFILE

(71) Applicant: NESTEC S.A., Vevey (CH)

(72) Inventors: Christophe Joseph Etienne Schmitt, Servion (CH); Etienne Pouteau, Lausanne (CH); Simina Florentina Popa Nita, Morges (CH); Laurence Donato-Capel, Cheseaux sur Lausanne (CH); Lionel Jean Rene Bovetto, Lucens (CH)

(73) Assignee: Nestec S.A., Vevey (CH)

( * ) Notice: Subject to any disclaimer, the term of this patent is extended or adjusted under 35 U.S.C. 154(b) by 86 days.

(21) Appl. No.: 15/527,804

(22) PCT Filed: Nov. 9, 2015

(86) PCT No.: PCT/EP2015/076074
§ 371 (c)(1),
(2) Date: May 18, 2017

(87) PCT Pub. No.: WO2016/078952
PCT Pub. Date: May 26, 2016

(65) Prior Publication Data
US 2018/0344772 A1    Dec. 6, 2018

(30) Foreign Application Priority Data
Nov. 19, 2014 (EP) ..................................... 14193824

(51) Int. Cl.
*A61K 35/20* (2006.01)
*A61P 3/10* (2006.01)
(Continued)

(52) U.S. Cl.
CPC .............. *A61K 35/20* (2013.01); *A23L 33/19* (2016.08); *A61K 9/1075* (2013.01); *A61P 3/10* (2018.01);
(Continued)

(58) Field of Classification Search
CPC .............................. A61K 35/20; A61K 31/715
See application file for complete search history.

(56) References Cited

U.S. PATENT DOCUMENTS 6,355,612 B1    3/2002  Ballevre et al.

FOREIGN PATENT DOCUMENTS

AU    2013231128    10/2013
EP    2074891       7/2009
(Continued)

OTHER PUBLICATIONS

Souza et al. "Production and characterization of microparticles containing pectin and whey proteins" Food Research International, 2012, vol. 49, pp. 560-566.
(Continued)

*Primary Examiner* — Rosanne Kosson
(74) *Attorney, Agent, or Firm* — K&L Gates LLP

(57) ABSTRACT

The present invention relates to a composition comprising polysaccharides and whey protein micelles for use in the treatment or prevention of a disorder linked to an increase in plasma postprandial insulin in a subject. The invention relates also to the non-therapeutic use of a composition comprising polysaccharides and whey protein micelles to decrease plasma postprandial insulin concentration. A further aspect of the invention is a process for forming polysaccharide-whey protein micelle complexes.

7 Claims, 4 Drawing Sheets

(51) Int. Cl.
*A23L 33/19* (2016.01)
*A61K 9/107* (2006.01)
*A61K 31/723* (2006.01)
*A61K 31/731* (2006.01)
*A61K 31/732* (2006.01)
*A61K 31/734* (2006.01)
*A61K 31/718* (2006.01)

(52) U.S. Cl.
CPC ..... *A23V 2002/00* (2013.01); *A23V 2200/328* (2013.01); *A23V 2250/5072* (2013.01); *A23V 2250/50366* (2013.01); *A23V 2250/54252* (2013.01); *A61K 31/718* (2013.01); *A61K 31/723* (2013.01); *A61K 31/731* (2013.01); *A61K 31/732* (2013.01); *A61K 31/734* (2013.01); *A61K 2300/00* (2013.01)

(56) References Cited

FOREIGN PATENT DOCUMENTS

| WO | 2004022074 | 3/2004 |
|---|---|---|
| WO | 2007073188 | 6/2007 |
| WO | 2010112430 | 10/2010 |
| WO | 2014140023 | 9/2014 |

OTHER PUBLICATIONS

Deat-Laine et al. "Efficacy of Mucoadhesive Hydrogel Microparticles of Whey Protein and Alginate for Oral Insulin Delivery" Pharm Res, 2013, vol. 30, pp. 721-734.

Gaaloul et al. "Rheological study of the effect of shearing process and k-carrageenan concentration on the formation of whey protein microgels at pH 7" Journal of Food Engineering, 2009, vol. 95, pp. 254-263.

USE OF WHEY PROTEIN MICELLES AND POLYSACCHARIDES FOR IMPROVING INSULIN PROFILE

CROSS REFERENCE TO RELATED APPLICATIONS

The present application is a National Stage of International Application No. PCT/EP2015/076074, filed on Nov. 9, 2015, which claims priority to European Patent Application No. 14193824.1 filed on Nov. 19, 2014, the entire contents of which are being incorporated herein by reference.

FIELD OF THE INVENTION

The present invention relates to a composition comprising polysaccharides and whey protein micelles for use in the treatment or prevention of a disorder linked to an increase in plasma postprandial insulin in a subject. The invention relates also to the non-therapeutic use of a composition comprising polysaccharides and whey protein micelles to decrease plasma postprandial insulin concentration. A further aspect of the invention is a process for forming polysaccharide-whey protein micelle complexes.

BACKGROUND OF THE INVENTION

Globally it is estimated that there are about 280 million people with type-2 diabetes. The incidence varies substantially in different parts of the world, almost certainly because of genetic, nutritional, environmental and lifestyle factors. In the USA, roughly 21 million patients are diagnosed as having diabetes, 90% of whom are type-2, with a further 8.1 million people estimated to be undiagnosed diabetes sufferers. Diabetes is the $7^{th}$ leading cause of death in the USA. The total cost of diabetes in the United States was $245 billion in 2012. Traditionally considered a disease of adults, type-2 diabetes is increasingly diagnosed in children in parallel to rising obesity rates due to alterations in dietary patterns as well as in life styles during childhood.

The primary early development of diabetes may appear when insulin response to a meal, or more specifically first-phase insulin release, becomes abnormal (Gerich J E, 2002, Diabetes, 51:S117-S121) and elevated blood glucose becomes unavoidable over time. Then chronic hyperglycemia generates an increased insulin demand and eventually a beta-cell secretory dysfunction causing exhaustion of the beta-cells in the pancreas (Porte D J, 2001, Diabetes Metab Res Rev, 17(3):181-188). This dysfunction of the insulin secretion is believed to appear in parallel to a defect of the hepatic and peripheral insulin action, identified as the insulin resistance which induces elevated fasting blood insulin. Enhanced insulin secretion and insulin resistance both cooperate to increase insulinemia and favour the development of type-2 diabetes. As a consequence, a diminished and adequate response of the insulinemia after a meal could be the sign of an adequate insulin secretion and utilization by the body in healthy or pre-diabetic subjects. This decreased postprandial insulinemia should preserve the pancreatic function and simultaneously improve insulin sensitivity. In the long term, lowering the insulin demand after a meal can reduce (1) the risk of developing type-2 diabetes in pre-diabetic subjects and (2) the deterioration of the glycemic control in type-2 diabetes.

Proteins are known to stimulate insulin secretion and a high protein diet has the potential to lower plasma glucose and fasting triglycerides in type-2 diabetic subjects [Van Loon L J et al., 2000, Am J Clin Nutr 72:96-105; Gannon M C et al., 2003, Am J Clin Nutr 78:734-741]. A recent study evaluated the acute effects of different protein types on postprandial lipemia after a fat-rich test meal in type-2 diabetic subjects [Mortensen L S et al., 2009, Am J Clin Nutr. 90:41-48]. Thereby, 4 iso-caloric meals with different protein sources, i.e. whey, casein, gluten and cod protein, were compared. It was concluded that whey proteins were most effective in reducing postprandial lipemia in those patients. A further study published by Shertzer H G et al. [2011, J Nutr 141:582-587] revealed that dietary whey protein isolates administered to mice reduced the risk for metabolic disease and of developing diabetes associated with the consumption of a high-fat diet.

WO2011/112695 discloses that health benefits provided by whey proteins include control of blood glucose such that they are suitable for diabetics. WO2013/057232 discloses that whey protein micelles may be used in the treatment or prevention of a disorder linked to an increase in plasma postprandial insulin in a subject.

There is a persisting need in the food industry to further improve the nutritional solutions provided to diabetic subjects, subjects at risk for developing diabetes and subjects with impaired glucose metabolism.

The object of the present invention is to improve the state of the art and to provide a new and better nutritional solution for improving the postprandial insulin profile in a subject, particularly in a diabetic or pre-diabetic subject.

The object of the present invention is achieved by the subject matter of the independent claims. The dependent claims further develop the idea of the present invention.

Accordingly, the present invention provides in a first aspect a composition comprising polysaccharides and whey protein micelles for use in the treatment or prevention of a disorder linked to an increase in plasma postprandial insulin in a subject wherein the polysaccharides have a negative zeta potential at a pH value in the range 2.5 to 4.5 and the weight ratio of whey protein micelles to polysaccharides is between 30:1 and 0.8:1.

In a further aspect, the invention pertains to a non-therapeutic use of a composition comprising polysaccharides and whey protein micelles to decrease plasma postprandial insulin concentration, wherein the polysaccharides have a negative zeta potential at a pH value in the range 2.5 to 4.5 and the weight ratio of whey protein micelles to polysaccharides is between 30:1 and 0.8:1.

In a still further aspect, the present invention pertains to a process for forming polysaccharide-whey protein micelle complexes comprising the steps of, (a) combining a polysaccharide with an aqueous dispersion of whey protein micelles to form a composition comprising an aqueous dispersion of polysaccharide and whey protein micelles, wherein the polysaccharide has a negative zeta potential at a pH value in the range 2.5 to 4.5 and the weight ratio of whey protein micelles to polysaccharide is between 30:1 and 0.8:1 (b) if the pH of the composition comprising an aqueous dispersion of polysaccharide and whey protein micelles is not already between 2.5 and 4.5, then adjusting the pH of the composition to between 2.5 and 4.5 to form polysaccharide-whey protein micelle complexes.

"Whey protein micelles" are defined herein as described in EP1839492A1. Particularly, the "whey protein micelles" are the micelles comprised in the whey protein micelles concentrate obtainable by the process as disclosed in EP1839492A1. Therein, the process for the production of whey protein micelles concentrate comprises the steps of: a)

adjusting the pH of a whey protein aqueous solution to a value between 3.0 and 8.0; b) subjecting the aqueous solution to a temperature between 80 and 98° C.; and c) concentrating the dispersion obtained in step b). Thereby, the micelles produced have an extremely sharp size distribution, such that more than 80% of the micelles produced have a size smaller than 1 micron in diameter and preferably are between 100 nm and 900 nm in size. The "whey protein micelles" can be in liquid concentrate or in powder form. Importantly, the basic micelle structure of the whey proteins is conserved, in the concentrate, the powder and reconstituted from the powder for example in water. The "whey protein micelles" are physically stable in dispersion, as powder as well as during spray-drying or freeze-drying.

"Insulin" is a hormone secreted by the beta cells of the pancreas in response to a meal. Insulin is central to regulating carbohydrate and fat metabolism in the body.

A high insulinogenic nutrition represents a chronic stimulus to the beta cells that may induce an adaptive hypertrophy and a progressive dysregulation of the cells, resulting in postprandial hyperinsulinemia. Postprandial hyperinsulinemia may promote weight gain, fat deposition and the development of insulin resistance, metabolic syndrome, glucose intolerance and type-2 diabetes (Kopp W., Metabolism. 2003, July; 52(7):840-844).

SUMMARY OF THE INVENTION

It has been surprisingly found by the inventors that consumption of compositions comprising polysaccharides and whey protein micelles decrease the postprandial plasma insulin response compared to the consumption of iso-caloric and iso-nitrogenous compositions having just whey protein isolate (WPI) or whey protein micelles (WPM) without polysaccharides. The results of a randomized double-blinded crossover pre-clinical study are disclosed in the Examples section. Previous studies have demonstrated that whey proteins in the form of WPI or WPM are effective in reducing postprandial insulin and reducing the risk for development of diabetes. Here, the inventors found an even better nutritional solution by providing the whey proteins in the form of compositions comprising polysaccharides and whey protein micelles for the desired health benefit. Consequently, postprandial plasma insulin concentrations can be lowered in comparison to WPI and WPM by providing compositions comprising a dispersion of polysaccharides and whey protein micelles as a still further benefit to diabetic and pre-diabetic subjects.

Although not wishing to be bound by theory, the inventors think that whey protein micelles together with polysaccharides induce a delayed gastric emptying or are more slowly digested than whey protein micelles alone.

DETAILED DESCRIPTION OF THE INVENTION

Figure 1:
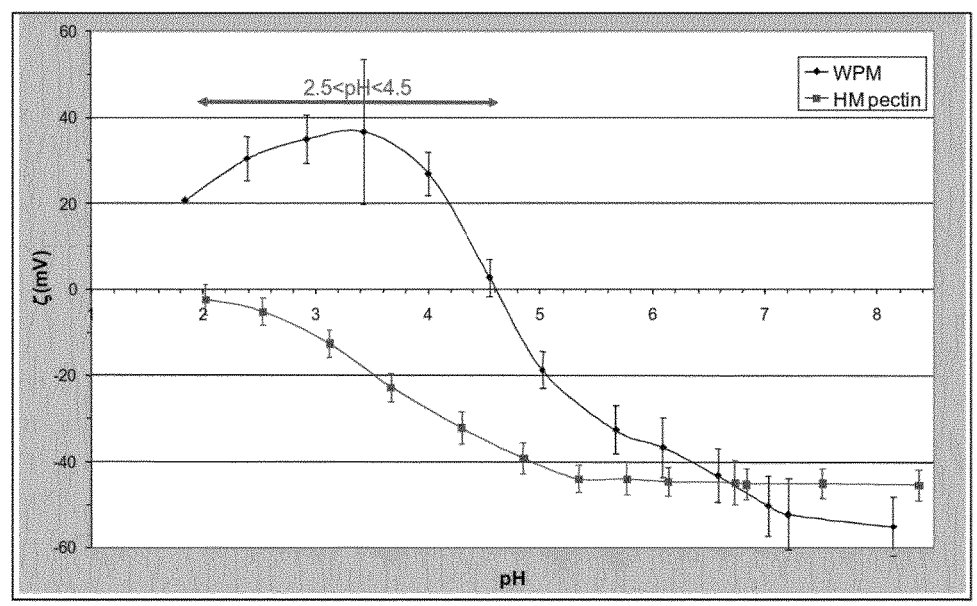
FIG. 1: Variation of surface charge ($\zeta$-potential) as a function of pH for WPM and pectin in solutions of concentration 0.1 wt. % and at T=25° C.

The present invention pertains to a composition comprising polysaccharides and whey protein micelles for use in the treatment or prevention of a disorder linked to an increase in plasma postprandial insulin in a subject wherein the polysaccharide has a negative zeta potential at a pH value in the range 2.5 to 4.5 and the weight ratio of whey protein micelles to polysaccharide is between 30:1 and 0.8:1. The whey protein micelles in the composition of the invention may be obtainable (for example obtained) by adjusting the pH of a whey protein aqueous solution to a value between 3.0 and 8.0 and subjecting the aqueous solution to a temperature between 80 and 98° C. For example, the whey protein micelles in the composition of the invention may be obtainable (for example obtained) by adjusting the pH of a demineralized native whey protein aqueous solution to a value between 5.8 and 6.6 and subjecting the aqueous solution to a temperature between 80 and 98° C. for a period of between 10 seconds and 2 hours.

The invention provides for the use of a composition comprising polysaccharides and whey protein micelles for the manufacture of a medicament for use in the treatment or prevention of a disorder linked to an increase in plasma postprandial insulin in a subject, wherein the polysaccharide has a negative zeta potential at a pH value in the range 2.5 to 4.5 and the weight ratio of whey protein micelles to polysaccharide is between 30:1 and 0.8:1.

Polysaccharides having a negative zeta ($\zeta$) potential have a negative surface charge. Polysaccharides having a negative zeta potential include alginate, xanthan, pectin, gum karaya, gum Arabic and carrageenan. The surface charge corresponding to the electrophoretic mobility, the zeta ($\zeta$) potential, of particles may be measured with a particle mobility distribution instrument such as a Zetasizer supplied by Malvern. The polysaccharides in the composition of the invention may have a negative zeta potential measured in the absence of sodium chloride. At pH values in the range 2.5 to 4.5, whey protein micelles have a positive zeta potential (positive surface charge) and thus, at these pH values, the whey protein micelles and polysaccharides carry opposite charges and can form electrostatic complexes. The pH range encountered during gastric digestion is between 2.5 and 4.0 and so, when the composition of the invention which is not already at a pH within this range is consumed, polysaccharide-whey protein micelle complexes are formed during gastric digestion. Alternatively, polysaccharide-whey protein micelle complexes may be formed by adjusting the pH of the composition to between 2.5 and 4.5 (for example between 3.8 and 4.2) before consumption. The polysaccharides and whey protein micelles comprised within the composition of the invention may be in the form of polysaccharide-whey protein micelle complexes. The polysaccharide-whey protein micelle complexes may be electrostatic complexes. The polysaccharides having a negative zeta potential at a pH value in the range 2.5 to 4 comprised within the composition of the invention may be selected from the group consisting of alginate, xanthan, pectin, gum karaya, gum Arabic and carrageenan. The polysaccharides comprised within the composition of the invention may be pectin (for example high methyl-esterified pectin) or carrageenan (for example λ-carrageenan).

The composition of the invention may contain at least 0.1 wt. %. whey protein micelles. The weight ratio of whey protein micelles to polysaccharide in the composition of the invention may be between 30:1 and 0.8:1, for example it may be between 10:1 and 1:1. The composition of the invention may have a protein content of between 0.1 and 22 wt. %, for example a whey protein content of between 0.1 and 22 wt. %.

Typically, postprandial hyper-insulinemia may promote the development of insulin resistance, metabolic syndrome, glucose intolerance and type-2 diabetes [Kopp W., Metabolism. 2003, July; 52(7):840-844]. Lowering the insulin demand after a meal however, can reduce on one hand the deterioration of the glycemic control in type-2 diabetes and on the other hand reduce the risk of developing type-2 diabetes in predisposed subjects. Hence, advantageously, the whey protein micelles are for use in the treatment or prevention of diabetes (for example type-2 diabetes or gestational diabetes), impairment of glucose metabolism, hyperinsulinemia or insulin resistance.

In an embodiment of the invention, the whey protein micelles are for use in a diabetic or pre-diabetic patient. A "pre-diabetic patient" is a subject showing insulin resistance or impaired glucose metabolism and is predisposed, for example by family history, lifestyle or genetics, for developing diabetes later in life. Reducing insulin secretion reduces the risk of the pancreas becoming exhausted in the long term, and so is beneficial for management of the pancreas in pre-diabetes or patients with metabolic disorders. The use of a composition comprising polysaccharides and whey protein micelles would consequently reduce the risk and/or the development of diabetes, impaired glucose metabolism, hyperinsulinemia or insulin resistance in those subjects.

Prevalence of diabetes, insulin resistance or glucose intolerance is mostly observed in adult humans. However, more and more children are affected, or predisposed or at risk of developing such a disorder later in life. Hence, advantageously, prevention and/or treatment of those disorders is started already in young age. Alternatively, and similarly as observed with humans; diabetes, hyperinsulinemia or insulin resistance are more and more widespread among animals, particularly with animals kept as pet animals. Hence, the invention also pertains to cats and dogs.

The composition for use according to the invention may be in any suitable format, for example the composition may be in the form of a bar, flakes or as pellets. The composition for use according to the invention may be a liquid composition. Liquids provide a convenient dose format, especially for patients who have difficulty chewing and swallowing solid foods. The composition for use according to the invention may be a liquid with a dynamic viscosity of less than 1 Pa·s at 20° C. For example the composition of the invention may be a liquid with a dynamic viscosity less than 0.5 Pa·s, for further example less than 0.3 Pa·s at 20° C.

The composition for use according to the invention may be provided in the form of a beverage, for example a liquid drink, a shake drink, a nutritional composition or a liquid meal replacement. Whey protein micelles have a more "milky" appearance compared to whey protein isolates. This can enhance the appearance of liquid drinks or meal replacers. The composition for use according to the invention may be a fermented milk product such as a yoghurt, for example a spoon-able yoghurt, a drinking yoghurt or a strained yoghurt. In the context of the present invention the term yoghurt may include, but is not limited to, materials complying with local food labelling regulations concerning the term "yoghurt".

Compositions comprising polysaccharides and whey protein micelles in solid form will be expected to form complexes in the acidic aqueous environment of the digestive system, but the formation of complexes is favoured by providing a composition in which the polysaccharides and whey protein micelles are an aqueous dispersion. The composition for use according to the invention may be a liquid composition comprising an aqueous dispersion of polysaccharides and whey protein micelles.

An important method of controlling food hygiene risks is to heat treat edible compositions which may harbour food pathogens or spoilage organisms. Well-known examples of such heat treatments are pasteurization, for example heating an edible material to 72° C. for 15 seconds, and ultra-high temperature (UHT) treatment, for example heating an edible material to above 135° C. for at least 2 seconds. It is advantageous that a liquid composition comprising an aqueous dispersion of polysaccharides and whey protein micelles will remain liquid after being heat treated. Heat treatment may be critical when the composition is to be administered to a subject with a weakened immunity to infection such as an elderly person or a patient in hospital. Generally, the protein content that can be included in heat sterilized liquid compositions is greatly limited. Compositions with high contents of protein form thick gels on heating and so do not provide a convenient liquid format once heat treated. For example a native whey protein dispersion forms a gel in the presence of 0.1 M of sodium chloride at a protein concentration of only 4% after a heat treatment 85° C. for 15 min. The addition of a polysaccharide would be expected to make the problem of gelling worse. For example, the addition of a polysaccharide such as pectin or carrageenan to whey protein has been found to decrease the protein gelling concentration or the gel time upon heat treatment [J. C. Harrington et al., Food Hydrocolloids, 23, 468-489 (2009)] [S. L. Turgeon et al., Food Hydrocolloids, 15, 583-591 (2001)]. The surprising finding that whey protein micelles may be heat treated in the presence of polysaccharides and still remain liquid therefore allows an advantageous liquid composition to be provided. The composition for use according to the invention permits a large quantity of protein to be delivered in a relatively small volume without bad taste or texture. The composition for use according to the invention may be a liquid composition and have a protein content between 0.1 and 22 wt. % and be a heat treated composition. For example, the composition for use according to the invention may be a heat treated liquid composition and have a protein content between 5 and 20 wt. %, for further example the composition for use according to the invention may be a heat treated liquid composition and have a protein content between 10 and 15 wt. %.

The composition for use according to the invention may be a liquid meal replacement, for example wherein the whey protein micelles are present in an amount of at least 1 wt. %, for example at least 10 wt. %, for further example at least 15 wt. % of the total dry weight of said liquid meal replacement. The liquid meal replacement may be for use in enteral nutrition. Thereby, advantageously, such a meal replacement can for example be used in intensive care units or hospitals, where patients due e.g. to their trauma are insulin resistant, but require a high protein diet for recovery. A liquid meal replacement thereby is very convenient and provides the required amounts of proteins in a well-adapted formulation. "Enteral nutrition" herewith is defined as a way to provide food or nutrition through a tube placed in the nose, the stomach or the small intestine. Enteral nutrition is often also called tube feeding. The composition may further comprise lipids and carbohydrates to provide appropriate nutrition.

The composition for use according to the invention may be administered in a daily dose to provide between 0.10 g and 0.75 g dry weight of whey protein micelles per 1 kg body weight, for example between 0.15 g and 0.5 g dry weight of whey protein micelles per 1 kg body weight. Those doses should assure a sufficient daily quantity for providing the desired effect to a subject in at least a mid-term period.

The composition for use according to the invention may be provided as part or at the end of a regular meal. For example, the composition may be provided as part or at the end of a meal to confer its benefits by reducing the insulin postprandial response in combination with that meal. An improved effect can be expected by providing the composition directly at the end of the meal, for example as part of the dessert.

A further aspect of the present invention is the non-therapeutic use of a composition comprising polysaccharides and whey protein micelles to decrease plasma postprandial insulin concentration, wherein the polysaccharides have a negative zeta potential at a pH value in the range 2.5 to 4.5 and the weight ratio of whey protein micelles to polysaccharide is between 30:1 and 0.8:1. The whey protein micelles in the composition used according to the invention may be obtainable (for example obtained) by adjusting the pH of a whey protein aqueous solution to a value between 3.0 and 8.0 and subjecting the aqueous solution to a temperature between 80 and 98° C. For example, the whey protein micelles in the composition used according to the invention may be obtainable (for example obtained) by adjusting the pH of a demineralized native whey protein aqueous solution to a value between 5.8 and 6.6 and subjecting the aqueous solution to a temperature between 80 and 98° C. for a period of between 10 seconds and 2 hours.

It is advantageous that a composition comprising polysaccharides and whey protein micelles can also be administered to subjects, for example healthy subjects, which may be at risk of developing diabetes type-2, insulin resistance or glucose intolerance at some later time. A composition comprising polysaccharides and whey protein micelles, as disclosed herein, provides a reduced insulin level after consumption. This effect is most favourable for limiting insulin demand and potential pancreas exhaustion, while providing at the same time a sufficient amount of a high quality protein (i.e. whey) for improving the general health status of those subjects.

The composition used non-therapeutically according to the invention may be a liquid composition comprising an aqueous dispersion of polysaccharides and whey protein micelles. The composition used non-therapeutically according to the invention may be a heat treated liquid composition and have a protein content of between 0.1 and 22 wt. %. For example, the composition used non-therapeutically according to the invention may be a heat treated liquid composition and have a protein content between 5 and 20 wt. %. The composition used non-therapeutically according to the invention may be a heat treated liquid composition and have a protein content greater than 10 wt. %, for example between 10 and 15 wt. %. It is advantageous that liquid compositions according to the invention may be heat treated, for example to preserve them during storage, without the protein forming thick gels or precipitates.

The composition used non-therapeutically according to the invention may comprise polysaccharides and whey protein micelles wherein the polysaccharide and whey protein micelles are in the form of polysaccharide-whey protein micelle complexes, for example electrostatic complexes. The composition used non-therapeutically according to the invention may be in the form of a beverage or yoghurt.

Another aspect of the invention provides a process for forming polysaccharide-whey protein micelle complexes (for example a process of manufacture of polysaccharide-whey protein micelle complexes) comprising the steps of;

a. forming whey protein micelles by adjusting the pH of a whey protein aqueous solution to a value between 3.0 and 8.0 and subjecting the aqueous solution to a temperature between 80 and 98° C.

b. combining polysaccharides with an aqueous dispersion of whey protein micelles to form a composition comprising an aqueous dispersion of polysaccharide and whey protein micelles, wherein the polysaccharides have a negative zeta potential at a pH value in the range 2.5 to 4.5 and the weight ratio of whey protein micelles to polysaccharide is between 30:1 and 0.8:1 c. if the pH of the composition comprising an aqueous dispersion of polysaccharide and whey protein micelles is not already between 2.5 and 4.5 (for example if the pH is not already between 3.8 and 4.2), then adjusting the pH of the composition to between 2.5 and 4.5 (for example between 3.8 and 4.2) to form a polysaccharide-whey protein micelle complex.

The formation of whey protein micelles in the process of the invention may be by adjusting the pH of a demineralized native whey protein aqueous solution to a value between 5.8 and 6.6 and subjecting the aqueous solution to a temperature between 80 and 98° C. for a period of between 10 seconds and 2 hours.

The composition comprising an aqueous dispersion of polysaccharides and whey protein micelles which is combined with polysaccharides may contain at least 0.1 wt. %. whey protein micelles. The weight ratio of whey protein micelles to polysaccharides in the composition comprising an aqueous dispersion of polysaccharides and whey protein micelles may for example be between 10:1 and 1:1. The polysaccharides in the composition comprising an aqueous dispersion of polysaccharides and whey protein micelles may have a negative zeta potential measured in the absence of sodium chloride. The composition comprising an aqueous dispersion of polysaccharides and whey protein micelles may be homogenized under pressure to ensure good dispersion.

The pH of the composition comprising an aqueous dispersion of polysaccharides and whey protein micelles may be adjusted by any known method, for example the pH may be adjusted by the addition of acids, bases (for example in the form of buffers) to the composition. Pre-forming complexes in this way leads to better control and can increase the amount of complex formed.

The pH of the composition may also be adjusted by the act of consuming the composition whereby it will encounter environments between pH 2.5 and 4.5, for example in the human lower stomach. The pH of the composition comprising an aqueous dispersion of polysaccharides and whey protein micelles may be adjusted to between 2.5 and 4.5 (for example between 3.8 and 4.2) by passing the composition into the digestive tract of a mammal. The polysaccharide-whey protein complex may be an electrostatic complex. The polysaccharides may be pectin or carrageenan.

The protein content of the composition comprising an aqueous dispersion of polysaccharides and whey protein micelles in the process of the invention may be between 0.1 and 22 wt. %, for example the protein content of the composition comprising an aqueous dispersion of polysaccharides and whey protein micelles in the process of the invention may be between 5 and 20 wt. %. The protein content may be greater than 10 wt. %, for example between 10 and 15 wt. %.

The process of the invention may further comprise the step of heat treatment. For example the process of the invention may further comprise heating the composition comprising an aqueous dispersion of polysaccharide and whey protein micelles to a temperature above 72° C. for a period of at least 3 seconds, for example above 135° C. for at least 3 seconds. The polysaccharides combined with an aqueous dispersion of whey protein micelles in the process of the invention may be selected from the group consisting of alginate, xanthan, pectin, gum karaya, gum Arabic, carrageenans and combinations of these. The polysaccharides may be pectin or carrageenan.

Those skilled in the art will understand that they can freely combine all features of the present invention disclosed herein. In particular, features described for the therapeutic use of the composition may be combined with the non-therapeutic use and vice versa. Further, features described for different embodiments of the present invention may be combined. Further advantages and features of the present invention are apparent from the figures and examples.

EXAMPLES

Example 1: Preparation of Pectin-Whey Protein Micelles Complexes

Electrostatic Complex Formation

Whey protein micelle powder (WPM) was produced by heat treatment at 85° C./15 min of a dispersion of whey protein isolate (Prolacta 90) at 4% wt protein at pH 5.89, then concentration by microfiltration up to 22% wt total solid and spray drying.

A pectin (high methyl-esterified pectin, Classic CU201, Herbstreith & Fox K G) stock solution of 5 wt. % was prepared in de-ionised water by stirring for 2-3 hours at 60° C. To allow complete hydration of the chains, the solution was stirred overnight at 4° C. A WPM stock solution of 15% wt and pH 3.5 was prepared. Firstly, the powder was dispersed in a 135 mM HCl solution, overnight at 4° C. The dispersion was then homogenized at 250 bars, 2 passes and at 50 bars, 1 pass. The final dry matter and subsequent protein concentration were verified using a HR73 Halogen Moisture Analyzer (Mettler Toledo) and the particle size was checked by dynamic light scattering (Zetasizer Nanoseries, Malvern, UK). Typical values were: hydrodynamic diameter Dh=300 nm, polydispersity index pdI=0.15. Mixes of different protein concentrations (range 0.1-10 wt. %) and WPM/pectin weight ratios (range 1:1-10:1) were obtained by blending the two solutions (and adding water if necessary). The mix was then homogenized at 500 bars for 2 passes at 25° C. Final pH of the system was adjusted to pH 4.0 using 1M NaOH.

Physicochemical Characterization of the Systems:

Surface Charge

The surface charge corresponding to the electrophoretic mobility, the ζ-potential, of the particles was measured with a particle mobility distribution instrument (Zetasizer Nano-series, Malvern, UK). A multipurpose titrator unit (MPT 2, Malvern) with 1M HCl and NaOH titrant solutions was used to vary the pH from 8 to 2 with an increment of 0.5 and a pH precision target of 0.3. A cell DTS1060C was used and the measurements were done at 25° C. 15 mL of 0.1% wt solution was employed. The data processing was done automatically.

Particle Size Distribution

Particle size distribution was measured using multi-angle static light scattering with a Mastersizer S long bench (Malvern, UK). Refractive indices of 1.36 for the disperse phase and 1.33 for the continuous phase and a backscattering index of 0.1 (3JHD presentation) were used in the calculation. Residual values were always lower than 1.5. Taking into account the arbitrary choice of the refractive index of the disperse phase and the mathematical model used (which assumes particles are spherical), present measurements only provide a qualitative indication of the aggregation in the systems rather than a quantitative determination of particle sizes.

Results

I. Identification of pH Conditions Allowing Formation of WPM/Pectin Electrostatic Complexes The surface charge (ζ-potential) of WPM and pectin as function of pH is illustrated in FIG. 1. As pH increased from 2 to 8, the ζ-potential of pectin decreased from neutral to −45 mV. This variation can be related to the carboxyl groups on the pectin backbone, At low pH, the neutralization of these groups induced ζ-potential values close to zero. For WPM, the ζ-potential varied from 20 mV at pH 2 to 40 mV at pH 3.8 and decreased to −45 mV at pH 8 with electroneutrality measured at pH 4.6. The latter can be related to the isoelectric point of β-lactoglobulin, the main constitutive protein of the WPM.

These results showed that in the pH range 2.5-4.5 the two components carried opposite charges and thus, are susceptible to forming electrostatic complexes.

II. Particle Size Distribution

Figure 2:
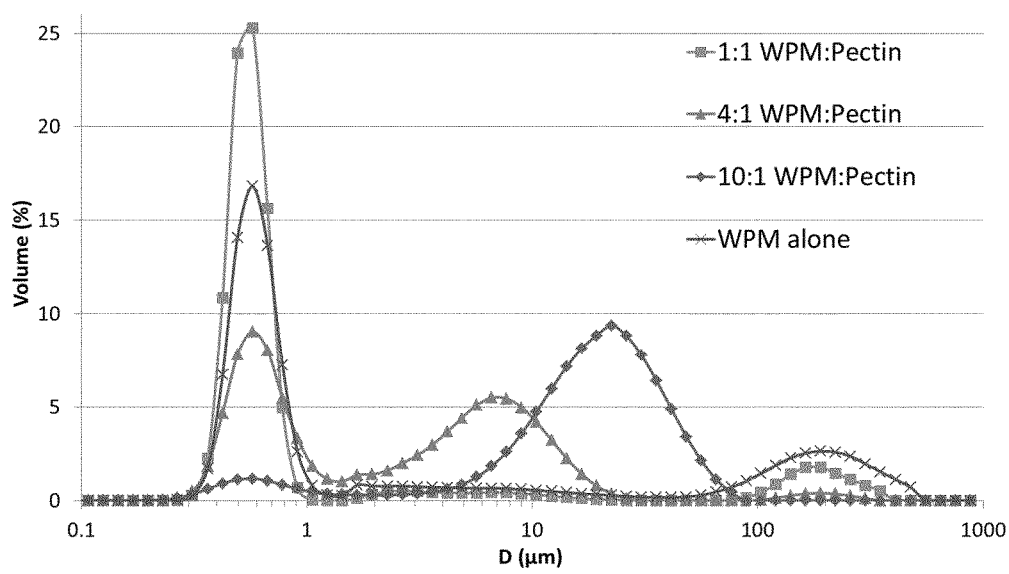
FIG. 2: Particle size distribution in WPM/pectin systems (at pH=4) of protein concentration of 1 wt. % and different pectin concentrations (weight ratios WPM:pectin between 1:1 and 10:1). Results are presented as scattered light intensity versus particle diameter in volume.
Figure 3:
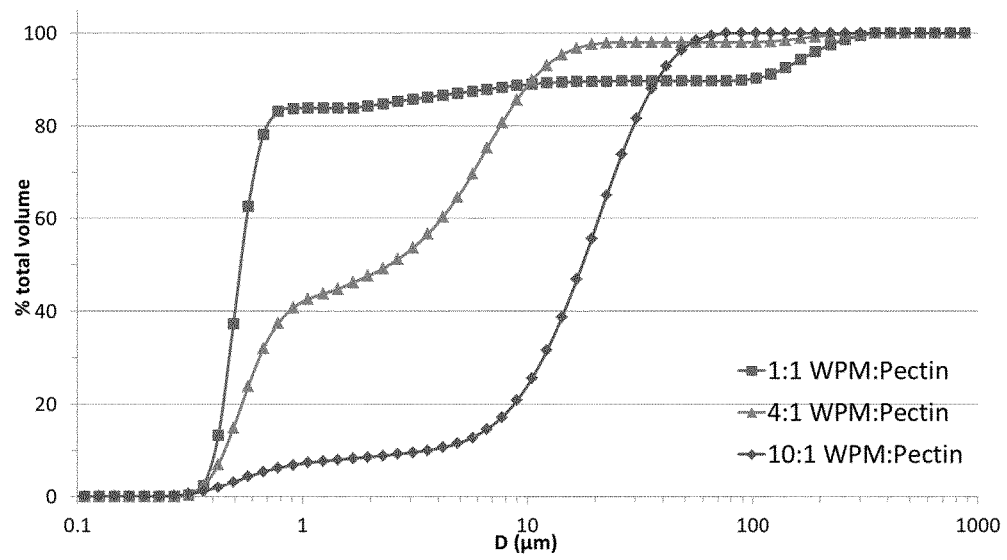
FIG. 3: Particle size distribution in WPM/pectin systems (at pH=4) of protein concentration of 1 wt. % and different pectin concentrations (weight ratios WPM:pectin between 1:1 and 10:1). Results are presented as percentage of total volume versus particle diameter.

In order to evaluate the variations induced by pectin addition to WPM, particle size distribution was measured and FIGS. 2 and 3 present the results obtained for systems containing 1 wt. % WPM and increasing amounts of pectin, from 0.1 wt. % to 1 wt. %, corresponding to WPM:pectin weight ratios of 10:1 to 1:1.

At low pectin concentration (0.1 wt. %), the mean diameter of the particles was higher than 10 μm and less than 10% of the total sample volume was represented by particles with diameters lower than 1 μm. As the pectin concentration increased up to 1 wt. %, the mean diameter decreased below 1 μm and more than 80% of the total volume was represented by particles with diameters lower than 1 μm. At pectin concentration of 1 wt. %, the average size of the particles was comparable to WPM alone. For high WPM:pectin ratios (i.e. low pectin concentrations), interactions between WPM and pectin are likely to occur due to charge effect and large aggregates are mainly formed. As pectin concentration increases, complexes comparable in size with WPM are formed probably due to compaction of pectin chains at the surface of the WPM.

The results show that an aqueous dispersion of pectin and whey protein micelles will form pectin-whey protein micelle complexes at pH conditions between 2.5 and 4.5.

Figure 4:
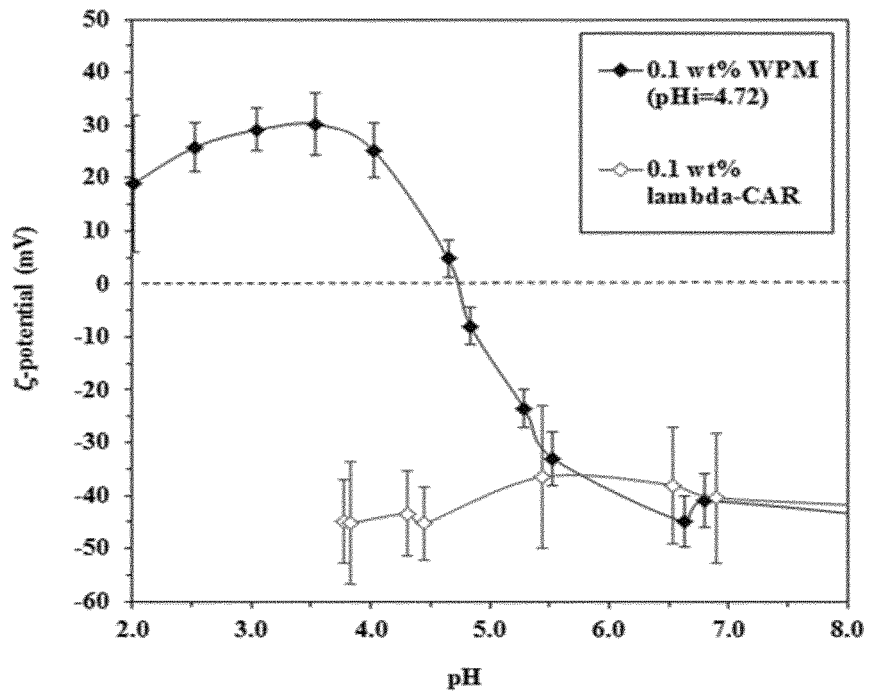
FIG. 4: Variation of the $\zeta$-potential of 0.1 wt. % whey protein micelles and $\lambda$-carrageenan as a function of pH as measured at 25° C. Vertical bars represent standard deviation. Horizontal dashed line represents particle electroneutrality.

Example 2: Complex Formation Between Whey Protein Micelles and λ-Carrageenan I. Identification of pH Conditions Allowing Formation of WPM/λ-Carrageenan Electrostatic Complexes λ-carrageenan (Benvisco CSP-82, Shemberg) dispersions were obtained by dispersing the required amount of powder in MilliQ™ water for 2 hours at room temperature. To ensure proper dispersion of the WPM, the WPM dispersions were homogenized at 250/50 bars. The ζ-potential of both WPM and λ-carrageenan (CAR) was determined as a function of pH in dilute conditions (FIG. 4). λ-carrageenan is a highly sulphated polysaccharide exhibiting high charge density (3 sulfate groups per sugar residue). λ-carrageenan behaves therefore as a strong acid with full dissociation of the sulphate groups independently from pH. This enables the formation of strong electrostatic complexes with WPM. As expected for a strong acid, the ζ-potential was constant and about −40/45 mV for all the pH range tested. As WPM exhibit a positive charge below pH 4.72, electrostatic complexes will be formed in gastric pH conditions, including the pH range 2.5-4.5.

II. Particle Size Distribution

Particle size was determined by dynamic light scattering using a Nanosizer ZS (Malvern Instruments, UK). WPM and CAR dispersions were mixed at 0.1 wt. % at various pH and mixing ratios and poured in squared plastic cuvettes (Sarstedt, Germany). Measurements were performed at 25° C. Depending on the sample turbidity the pathlength of the light was set automatically by the apparatus. The autocorrelation function G2(t) was calculated from the fluctuation of the scattered intensity with time. From the polynomial fit of the logarithm of the correlation function using the "cumulants" method, the z-average hydrodynamic diameter of the particles was calculated assuming that the diffusing particles were monodisperse spheres.

Figure 5:
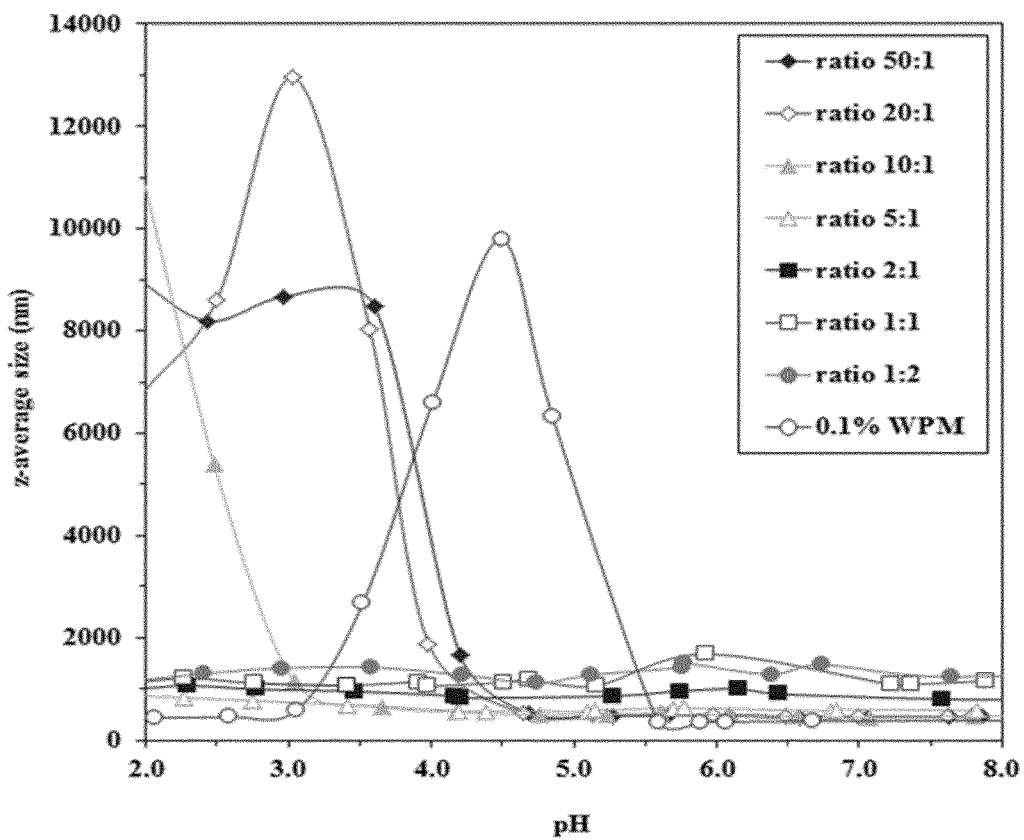
FIG. 5: z-average diameter of 0.1 wt. % WPM/$\lambda$-carrageenan complexes as a function of pH at 25° C.

WPM and CAR dispersions were mixed at 0.1 wt. % at various pH and mixing ratios. WPM exhibit an average diameter of 250 nm at extreme pH and tend to aggregate close to their IEP around pH 4.5 (FIG. 5). Upon addition of CAR, the size of the complexes increases drastically for mixing ratios of 50:1, 20:1 and 5:1. This large size in general leads to the rapid sedimentation of the complexes. For higher mixing ratios (excess CAR) the apparent diameter of the complexes slightly increased to 1 μm compared to WPM, but remained constant on the whole pH range.

Example 3: Influence of Whey Protein Micelles and Polysaccharide on Insulin Production The inventors monitored the postprandial response of insulin in a randomized double-blinded crossover study in healthy minipigs. A wash-out period of at least 6 days was observed between two meals and during this time, minipigs were given regular diet.

The following iso-caloric and iso-nitrogenous meals were compared.

| | |
|---|---|
| A | Whey protein isolate (WPI) + lipids + maltodextrin |
| B | Whey protein micelles (WPM) + lipids + maltodextrin |
| C | Whey protein micelles (WPM) + lipids + maltodextrin + carrageenan |
| D | Whey protein micelles (WPM) + lipids + maltodextrin + pectin |

All meals were approximately 300 mL and contained 30 g of the protein (WPI or WPM), 11 g of lipid and 30 g of maltodextrin. Meal C contained 1.5 g of λ-carrageenan (Benvisco CSP-82, Shemberg Corp.) and meal D contained 3 g pectin (high methyl-esterified pectin, Classic CU201, Herbstreith & Fox K G). The calorific value and protein content were measured analytically and the size of each test meal slightly adjusted to ensure they were all iso-caloric and iso-nitrogenous. Meals A, B and C were at neutral pH and Meal D was at acidic pH. The composition comprising λ-carrageenan and WPM (meal C) was kept at a pH outside the range 2.5 to 4.5 so that complexes between λ-carrageenan and WPM would not form in the meal. Complexes will only form once the meal passes into the low pH regions of the digestive system of the minipig. Complexes between λ-carrageenan and WPM have been found to have low colloidal stability and would cause undesirable precipitation if they formed in the liquid composition. In contrast, the complexes between pectin and WPM formed at pH 4 in meal D have good colloidal stability and so can already be present in the liquid composition before it is consumed by the minipigs.

Meal A: WPI (Prolacta 90) was mixed with a homogenised emulsion of 40% oil in water stabilized by 4% Citrem emulsifier. Maltodextrin (DE 21) was added, and the mixture underwent UHT treatment at 148° C. for 3 seconds before filling into sterile bottles.

Meal B: WPM powder was produced by heat treating a 4 wt. % protein dispersion (pH 5.89) of WPI (Prolacta 90) at 85° C. for 15 minutes, then concentration by microfiltration up to 22 wt. % solids and spray drying. A 15% t.s. solution (pH 7) of WPM was homogenised and mixed with a homogenised emulsion of 40% oil in water stabilized by 4% Citrem emulsifier. Maltodextrin (DE 21) was added, and the mixture underwent UHT treatment at 148° C. for 3 seconds before filling into sterile bottles.

Meal C: WPM powder was produced as for meal B. A 15% t.s. solution (pH 7) of WPM was homogenised and mixed with λ-carrageenan and maltodextrin at 60° C. for 1 hour before being homogenized at 250 bar and mixed with a homogenised emulsion of 40% oil in water stabilized by 4% Citrem emulsifier. The pH was is checked/adjusted to be pH 7. The mixture underwent UHT treatment at 148° C. for 3 seconds before filling into sterile bottles.

Meal D: WPM powder was produced as for meal B. A 15% t.s. solution (pH 4) of WPM was homogenised and mixed with pectin and maltodextrin at 60° C. for 1 hour before being homogenized at 250 bar and mixed with a homogenised emulsion of 40% oil in water stabilized by 4% Citrem emulsifier. The pH was checked/adjusted to be pH 4. The mixture underwent UHT treatment at 148° C. for 3 seconds before filling into sterile bottles.

Figure 6:
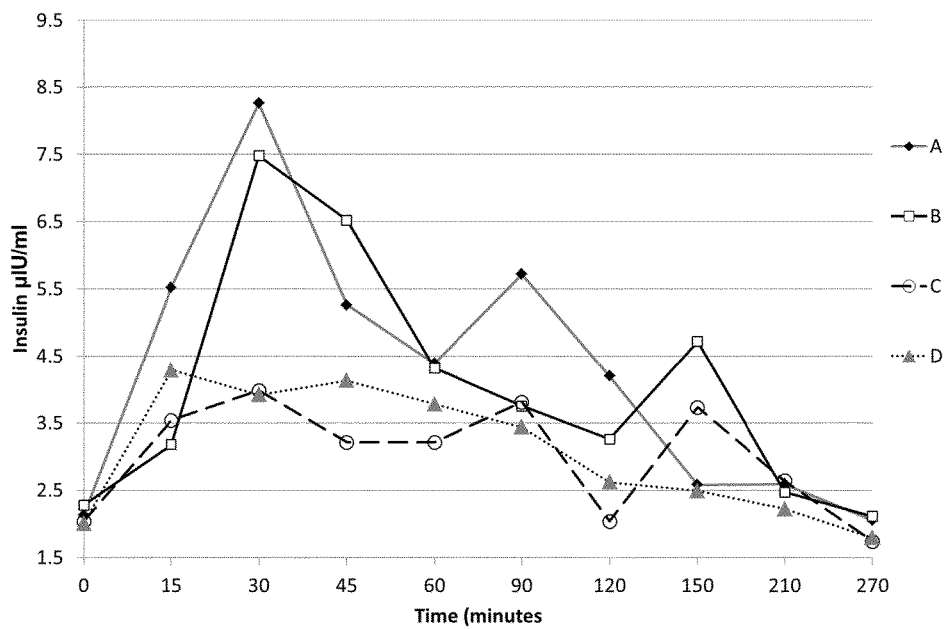
FIG. 6: Plasma concentrations of aorta insulin after the ingestion of meal by minipigs.
Figure 7:
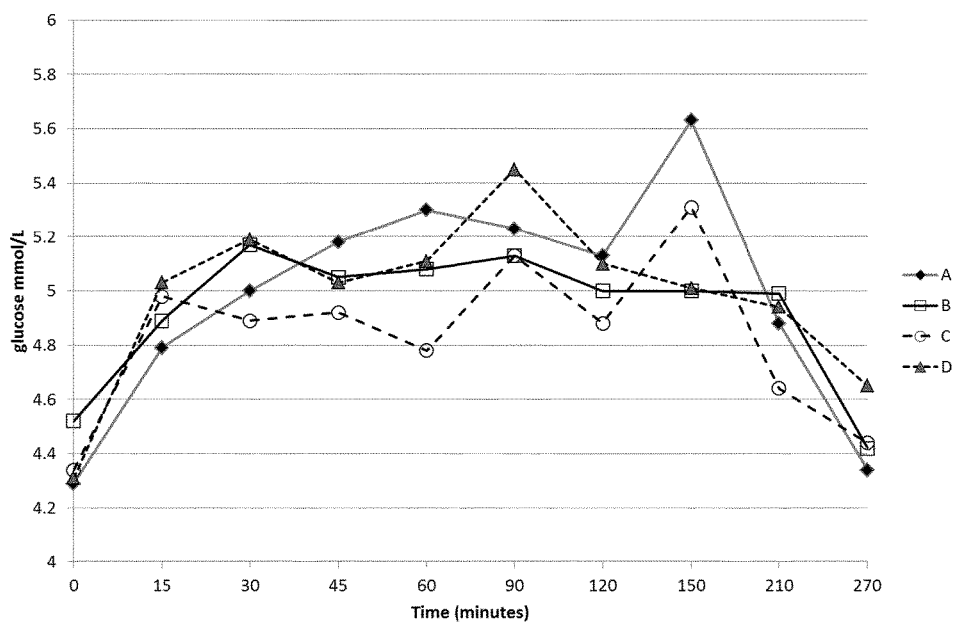
FIG. 7: Plasma concentrations of aorta glucose after the ingestion of meal by minipigs.

Blood samples were taken at 11 time points from 30 minutes before the meal to 270 minutes after, and the plasma insulin (FIG. 6) and glucose (FIG. 7) determined. It can be seen that the postprandial insulin response is lower for the meals comprising WPM/carrageenan (C) and WPM/pectin (D) than for the meals containing either WPI (A) or WPM (B) without polysaccharide, while the glucose clearance was essentially the same. This demonstrates that less insulin was required to clear glucose from the blood after meals of polysaccharide and WPM than for meals of WPM or WPI alone, the postprandial glucose response inducing lower insulin. This study showed the advantage of aqueous dispersions of polysaccharide and WPM for lowering plasma insulin.

The invention claimed is:

1. A method for treating a disorder linked to an increase in plasma postprandial insulin in a subject in need of same, comprising administering to the subject a composition comprising polysaccharides and whey protein micelles, wherein the polysaccharides have a negative zeta potential at a pH value in the range of 2.5 to 4.5, wherein the weight ratio of the whey protein micelles to the polysaccharide is between 30:1 and 0.8:1, and wherein the whey protein micelles are obtainable by adjusting the pH of a whey protein aqueous solution to a value between 3.0 and 8.0 and subjecting the aqueous solution to a temperature between 80 and 98° C.

2. The method according to claim 1 wherein the disorder is selected from the group consisting of diabetes; impairment of glucose metabolism; hyperinsulinemia; and insulin resistance.

3. The method according to claim 1 wherein the subject is a diabetic or pre-diabetic patient.

4. The method according to claim 1 wherein the composition is a liquid composition comprising an aqueous dispersion of polysaccharides and whey protein micelles.

5. The method according to claim 4, wherein the protein content of the composition is between 0.1 and 22 wt. % and wherein the composition is a heat treated composition.

6. The method according to claim 1 wherein the polysaccharides and whey protein micelles are in the form of polysaccharide-whey protein micelle complexes.

7. The method according to claim 1 wherein the composition is in the form of a beverage or yoghurt.

* * * * *